(12) United States Patent
Van Der Wilt

(10) Patent No.: US 9,976,969 B1
(45) Date of Patent: May 22, 2018

(54) MONITORING METHOD AND APPARATUS FOR EXCIMER-LASER ANNEALING PROCESS

(71) Applicant: Coherent LaserSystems GmbH & Co. KG, Göttingen (DE)

(72) Inventor: Paul Van Der Wilt, Göttingen (DE)

(73) Assignee: Coherent LaserSystems GmbH & Co. KG, Göttingen (DE)

( * ) Notice: Subject to any disclaimer, the term of this patent is extended or adjusted under 35 U.S.C. 154(b) by 0 days. days.

(21) Appl. No.: 15/477,311

(22) Filed: Apr. 3, 2017

Related U.S. Application Data

(60) Provisional application No. 62/415,357, filed on Oct. 31, 2016, provisional application No. 62/414,431, filed on Oct. 28, 2016.

(51) Int. Cl.
| | |
|---|---|
| *G01J 3/00* | (2006.01) |
| *G01N 21/958* | (2006.01) |
| *H04N 7/18* | (2006.01) |
| *G01N 21/27* | (2006.01) |
| *H01S 3/00* | (2006.01) |
| *H01S 3/225* | (2006.01) |
| *G01N 21/84* | (2006.01) |

(52) U.S. Cl.
CPC .......... *G01N 21/958* (2013.01); *G01N 21/27* (2013.01); *H04N 7/183* (2013.01); *G01N 2021/8477* (2013.01); *H01S 3/005* (2013.01); *H01S 3/225* (2013.01)

(58) Field of Classification Search
CPC .......... G01J 3/02; G01N 21/958; G01N 21/27; G01N 21/31; G01N 21/55; G01N 21/64; G01N 21/65; G01N 21/87; G01N 21/88; H04N 7/18
See application file for complete search history.

(56) References Cited

U.S. PATENT DOCUMENTS

| | | | |
|---|---|---|---|
| 4,696,536 | A | 9/1987 | Albares et al. |
| 4,806,018 | A | 2/1989 | Falk |
| 4,810,047 | A | 3/1989 | Pernick |
| 5,432,607 | A | 7/1995 | Taubenblatt |
| 5,473,426 | A | 12/1995 | Hayano et al. |
| 6,429,943 | B1 | 8/2002 | Opsal et al. |
| 6,639,201 | B2 | 10/2003 | Almogy et al. |
| 7,061,623 | B2 | 6/2006 | Davidson |

(Continued)

FOREIGN PATENT DOCUMENTS

| | | |
|---|---|---|
| CN | 101855091 A | 10/2010 |
| EP | 3081901 A1 | 10/2016 |

(Continued)

OTHER PUBLICATIONS

Final Office Action received for U.S. Appl. No. 13/907,637, dated Mar. 24, 2017, 35 pages.

(Continued)

*Primary Examiner* — Abdullahi Nur
(74) *Attorney, Agent, or Firm* — Morrison & Foerster LLP

(57) ABSTRACT

A method of evaluating a crystallized silicon layer on a substrate includes injecting light into the substrate in such a way that it is wave-guided by the substrate. Wave-guided injected light is diffracted out of the substrate by periodic features of the silicon layer. The diffracted light is detected and processed to evaluate the crystalline layer.

20 Claims, 5 Drawing Sheets

(56) References Cited

U.S. PATENT DOCUMENTS

| | | |
|---|---|---|
| 7,723,169 B2 | 5/2010 | Graefe et al. |
| 9,335,276 B2 | 5/2016 | Van Der Wilt |
| 2002/0140930 A1 | 10/2002 | Lin et al. |
| 2003/0017658 A1 | 1/2003 | Nishitani et al. |
| 2003/0227618 A1 | 12/2003 | Some |
| 2004/0125375 A1 | 7/2004 | Some |
| 2005/0002016 A1 | 1/2005 | Tsao |
| 2006/0060130 A1 | 3/2006 | Im |
| 2006/0131289 A1 | 6/2006 | Jyumonji et al. |
| 2007/0173039 A1 | 7/2007 | Tagusa |
| 2007/0196967 A1 | 8/2007 | Graefe et al. |
| 2008/0037005 A1 | 2/2008 | Bareket et al. |
| 2008/0297783 A1 | 12/2008 | Urano et al. |
| 2009/0002687 A1 | 1/2009 | Wenzel |
| 2010/0093112 A1 | 4/2010 | Takagi et al. |
| 2010/0098592 A1* | 4/2010 | Rong ............... G01N 21/552 422/82.11 |
| 2010/0112790 A1 | 5/2010 | Sugahara et al. |
| 2013/0341310 A1 | 12/2013 | Van Der Wilt |
| 2015/0247808 A1 | 9/2015 | Van Der Wilt |

FOREIGN PATENT DOCUMENTS

| | | |
|---|---|---|
| JP | 10-300662 A | 11/1998 |
| JP | 2001-110861 A | 4/2001 |
| JP | 2003-318240 A | 11/2003 |
| JP | 2004-172424 A | 6/2004 |
| JP | 2005-191173 A | 7/2005 |
| JP | 2008-268141 A | 11/2008 |
| JP | 2013-258181 A | 12/2013 |

OTHER PUBLICATIONS

Final Office Action received for U.S. Appl. No. 14/195,656 dated Nov. 16, 2015, 7 pages.
International Preliminary Report on Patentability received for PCT Application No. PCT/EP2015/054326, dated Sep. 15, 2016, 8 pages.
International Preliminary Report on Patentability received for PCT Patent Application No. PCT/EP2013/062883 dated Dec. 31, 2014, 8 pages.
International Search Report and Written Opinion received for PCT Patent Application No. PCT/EP2013/062883 dated Sep. 23, 2013, 9 pages.
International Search Report and Written Opinion received for PCT Patent Application No. PCT/EP2015/054326, dated May 27, 2015, 9 pages.
Leonhardt et al., "Removing Ambiguities in Surface Roughness Measurement", Optica Acta, vol. 29, No. 4, 1982, pp. 493-499.
Non Final Office Action received for U.S. Appl. No. 14/195,656, dated Apr. 23, 2015, 10 pages.
Non-Final Office Action received for U.S. Appl. No. 13/907,637, dated Nov. 1, 2016, 25 pages.
Notice of Allowance received for Taiwanese Patent Application No. 102122172, dated Oct. 28, 2016, 4 Pages (1 page of English Translation and 3 pages of Official Copy).
Notice of Allowance received for U.S. Appl. No. 14/195,656, dated Jan. 26, 2016, 8 pages.
Office Action received for Chinese Patent Application No. 201380032696.X, dated Jun. 14, 2016, 15 Pages (8 pages of English Translation and 7 Pages of Official Copy).
Office Action received for Japanese Patent Application No. 2015-517763, dated Jan. 4, 2017, 6 pages (3 Pages of English Translation and 3 pages of Official Copy).
Hill et al., "Waveguide Scattering Microscopy for Dark-Field imaging and Spectroscopy of Photonic Nanostructures", ACS Photonics, vol. 1, 2014, pp. 725-731.
International Search Report and Written Opinion received for PCT Patent Application No. PCT/EP2017/077514, dated Jan. 17, 2018, 14 pages.

* cited by examiner

MONITORING METHOD AND APPARATUS FOR EXCIMER-LASER ANNEALING PROCESS

PRIORITY CLAIM

This application claims priority of U.S. Provisional Patent Application No. 62/414,431, filed Oct. 28, 2016 and U.S. Provisional Patent Application No. 62/415,357, filed Oct. 31, 2016, the entire disclosures of which are incorporated herein by reference.

TECHNICAL FIELD OF THE INVENTION

The present invention relates in general to melting and recrystallization of thin silicon layers by pulsed laser irradiation. The invention relates in particular to methods of evaluating the recrystallized layers.

DISCUSSION OF BACKGROUND ART

Flat panel displays are an enabling technology for all contemporary portable consumer electronic devices and large-format televisions. Silicon (Si) crystallization is a processing step that is often used in the manufacture of thin-film transistor (TFT) active-matrix liquid-crystal displays (AMLCDs) and active-matrix organic light-emitting diode (AMOLED) displays. Crystalline silicon forms a semiconductor base, in which electronic circuits of the display are formed by conventional lithographic processes.

Commonly, crystallization is performed using a pulsed beam of laser-radiation that is shaped into the form of a long line having a uniform intensity profile along the length direction (long-axis) and a uniform or "top-hat" intensity profile across the width direction (short-axis). In the crystallization process, a thin layer of amorphous silicon (a "silicon film") on a glass substrate is repeatedly melted by the pulsed laser-radiation, while the substrate and the silicon layer thereon are translated relative to a source and optics delivering the pulsed laser-radiation. Repeated melting and re-solidification (recrystallization) through exposure to the pulsed laser-radiation, at a certain optimum energy-density, take place until a desired crystalline microstructure is obtained in the silicon film.

Optical elements are used to form the pulsed beam of laser-radiation into a long line on the silicon film. Crystallization occurs in a strip having the length and width of the long line of laser-radiation. Every effort is made to keep the intensity of the pulsed laser-radiation highly uniform along the long line. This effort is necessary to keep the crystalline microstructure uniform along the strip. A favored source of the pulsed laser-radiation is an excimer laser, which delivers laser-radiation having a wavelength in the ultraviolet region of the electromagnetic spectrum. The above described crystallization process, using excimer-laser pulses, is usually referred to as excimer-laser annealing (ELA). The process is a delicate one. The error margin for the optimum energy-density can be a few percent or even as small as ±0.5%.

There are two modes of ELA. In one mode, the translation speed of a panel relative to the laser beam is sufficiently slow that the "top-hat portion" of the beam-width overlaps by as much as 95% from one pulse to the next, so any infinitesimal area receives a total of about 20 pulses. In another mode, referred to as advanced ELA (AELA), the translation speed is much faster and in a single pass over a panel the irradiated "lines" have minimal overlap and may even leave un-crystallized space therein between. Multiple passes are made such that the entire panel is irradiated with a total number of pulses that may be less than in an ELA process to produce equivalent processed material.

Evaluation of crystallized silicon films on panels in a production line is often done off-line, by visual inspection. In particular, panels are checked for undesirable periodic features formed in the silicon film during ELA and AELA processes when the energy density of the crystalizing beam becomes non-optimal. Visual inspection is entirely subjective and relies on highly-trained inspectors, who through their experience are able to correlate observed features in the panels with very small changes in the crystallizing beam, for example, with a less than 1% change in energy-density. In a manufacturing environment, the process of visual analysis to determine if a change of process energy-density is required typically takes between about one hour and one and one-half hours from when the crystallization was performed, with a corresponding adverse effect on the throughput of acceptable panels in a production line.

An on-line method of evaluating crystallized silicon films on panels is described in U.S. Pat. No. 9,335,276, assigned to the assignee of the present invention, and the complete disclosure of which is incorporated herein by reference. In this method a microscope image of a portion of a panel is used for the evaluation. The image is formed from light diffracted from periodic features formed in the recrystallized silicon films by the ELA process. Measured contrast of structure in the diffraction image is one method used to evaluate the annealing process.

A shortcoming of this method is that reflected light from a light source illuminating the panel must be excluded from the microscope objective to provide the diffraction image. This can be done by using a physical stop or by using crossed polarizers between the panel and the microscope. As neither method is completely effective, there is some "softening" or reduction in contrast in the diffraction image. There is a need for a method of evaluating crystallized layers using light diffracted from the layers, wherein the illumination source is de-coupled from a detector measuring the diffracted light.

SUMMARY OF THE INVENTION

In one aspect, a method in accordance with the present invention for detecting periodic features in a surface of a recrystallized silicon layer provided on a substrate, comprises coupling light into the substrate such that at least a portion of the light is wave-guided by the substrate and coupled out of the substrate. The light coupled out of the substrate is monitored to determine properties of the periodic features.

The light may be coupled into the substrate via an edge thereof and coupled out of the substrate at the surface thereof by the periodic features. Alternatively, the light may be coupled into the substrate at the surface thereof by the periodic features, and coupled out of the substrate at an edge thereof. The light may also be coupled into the substrate at a first location of the surface of the substrate by the periodic features, and coupled out of the substrate at a second location of the surface of the substrate by the periodic features.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

DETAILED DESCRIPTION OF THE INVENTION

Figure 1:
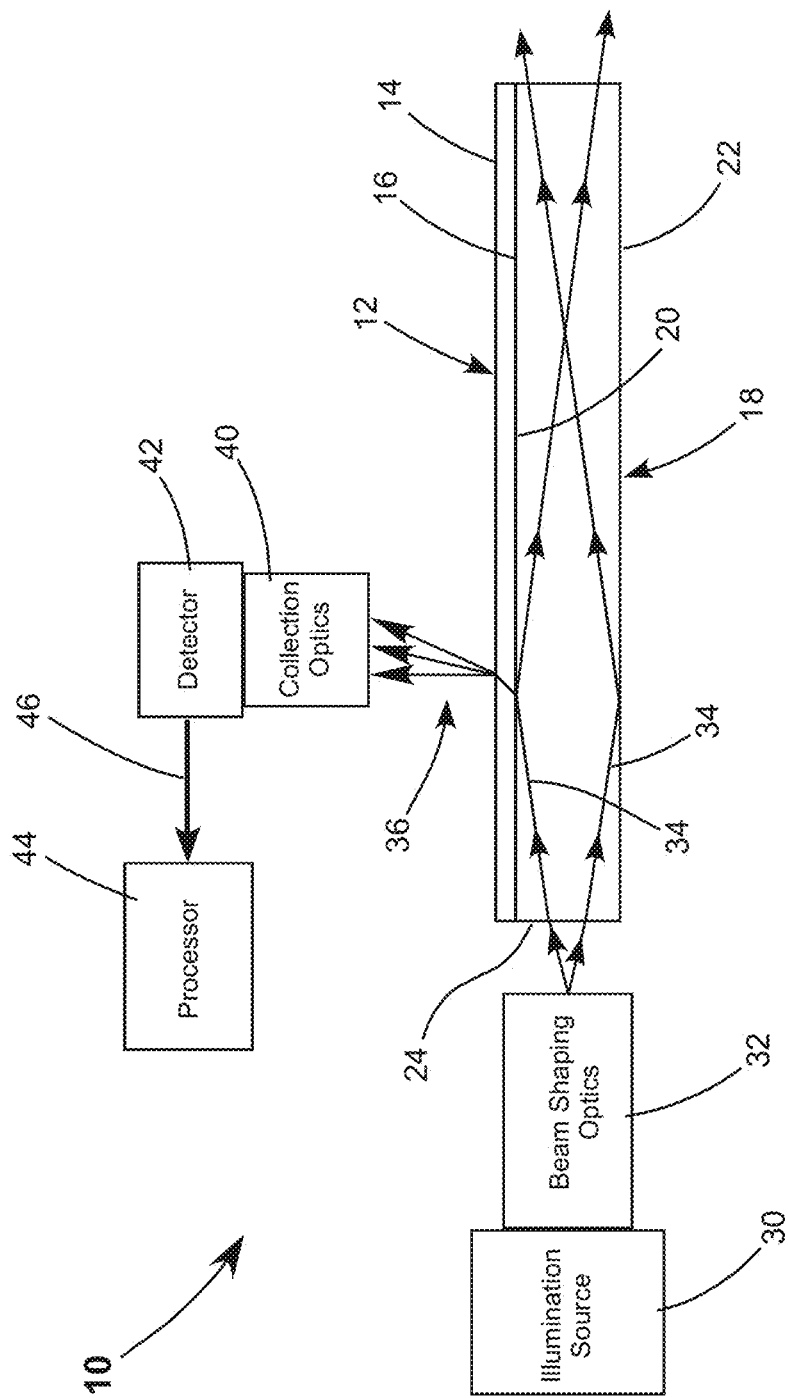
FIG. 1 schematically illustrates one preferred embodiment of the present invention for evaluating a silicon layer on a transparent substrate, including an illumination source and beam-shaping optics directing light into the substrate via an edge thereof, collection optics for collecting a portion of the light diffracted out of the substrate by the silicon layer, and a detector element and processor for monitoring the diffracted light portion.

Turning now to the drawings, wherein like features are designated by like reference numerals, FIG. 1 schematically illustrates one preferred embodiment 10 of the present invention for evaluating a silicon layer 12 on a substrate 18. By way of example, substrate 18 could be made of a glass. There may be other layers between the silicon layer and the substrate. Silicon layer 12 has upper surface 14 and lower surface 16. Substrate 18 has upper surface 20 and lower surface 22. It is assumed that silicon layer 12 is being annealed (recrystallized) by laser-radiation from an excimer laser (not shown). It is further assumed that the substrate and the silicon layer thereon are being translated relative to the excimer laser, in this instance, in a direction perpendicular to the plane of the drawing.

Beam-shaping optics 32 direct light from an illumination source 30 into substrate 18 through an edge 24 thereof. Illumination source 30 generates light to which the substrate is substantially transparent, preferably visible light and that is assumed in this description. That light may be monochromatic or have a broad range of wavelengths. One suitable light source is a flash-lamp. Another suitable light source is a white-light light-emitting diode (LED) array. From the description provided herein, those skilled in the art may use other light sources without departing from the spirit and scope of the present invention.

Light rays 34 from illumination source 30 and beam-shaping optics 32 entering the substrate that have sufficiently-low numerical aperture (NA) and are incident on lower surface 22 undergo total internal reflection. Light rays 34 incident on upper surface 20 of the substrate are partially reflected and partially transmitted because of the high refractive index of the silicon layer (about 4.15 at a wavelength of 530 nanometers) relative to that of the substrate (about 1.52 at a wavelength of 530 nanometers for a glass substrate). In effect, the substrate acts as a waveguide or light-guide for light rays 34.

At any location having periodic features introduced into silicon layer 12 by the excimer-laser annealing (recrystallization) process, light rays 34 incident on upper surface 20 and transmitted into silicon layer 12 are diffracted by the periodic features. Light rays 34 that are not transmitted and diffracted remain guided by the substrate, thereby achieving the desired decoupling of the illumination source from a detector. If the light rays have a range of wavelengths, diffracted rays 36 will propagate from the silicon layer over a range of wavelength-dependent angles, as depicted. For example, when using an illumination source 30 producing white light, diffracted rays 36 will be spectrally dispersed. "Location" means, here, a portion of the area of silicon layer 12.

Collection optics 40 receive diffracted rays 36 and direct the diffracted rays to a detector 42, which may include one detector element or an array of detector elements. Detector 42 converts an optical image formed by collection optics 40 into an electrical signal 46. Electrical signal 46 from detector 42 is received and interpreted by a processor 44 to obtain a numerical representation of the condition of silicon layer 12. By way of example, collection optics 40 could be an optical microscope, detector 42 could be a digital camera, and electrical signal 46 could be a digitized image. Possible criteria to evaluate the condition of the silicon layer include contrast and spectral content.

It is pointed out here that in FIG. 1, and in drawings of other embodiments of the present invention discussed further hereinbelow, only sufficient rays are depicted to describe principles of the present invention. In detail, light rays 34 transmitted into silicon layer 12 are diffracted by periodic features in upper surface 14. These periodic surface features closely match periodicities in the underlying crystalline grain structure of the recrystallized silicon layer. In practice, diffracted rays 36 can emanate from a large area of the silicon-layer surface, allowing the detector to record an image of that whole area.

Further, it should be noted that at a detailed description of beam-shaping optics 32 and collection optics 40 is not necessary for understanding principles of the present invention, and accordingly is not presented herein. Suitable optical arrangements would be evident to one skilled in the optical engineering art, which would depend on the light source and detector selected. Also, while the collection optics and detector are depicted as being directed normally to the substrate and silicon film thereon, the optics and detector may be directed non-normally to capture a selected wavelength or to optimize capture of the diffracted light.

Figure 2:
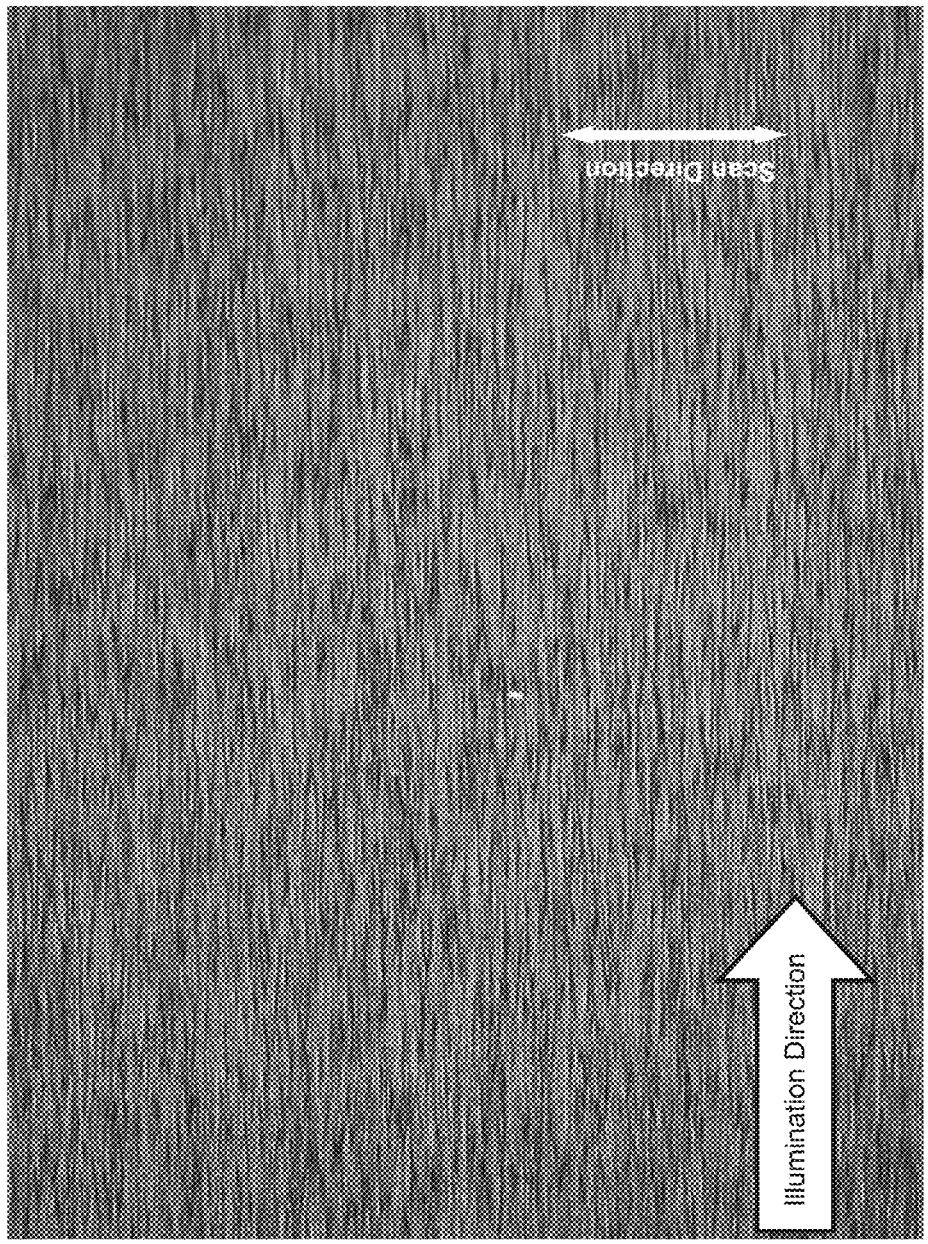
FIG. 2 schematically illustrates an orthoscopic microscope image of an excimer-laser recrystallized silicon layer taken using apparatus similar to the apparatus of FIG. 1.

FIG. 2 schematically illustrates an orthoscopic microscope image of an excimer-laser recrystallized silicon layer obtained using apparatus similar to the apparatus of FIG. 1. The light source was a lamp, producing white light as pulses having a duration of about 300 milliseconds (ms). The microscope was fitted with a 20× objective. The direction of light injection into the substrate and the scan direction of the substrate relative to incident laser-radiation is indicated on the drawing. The image is depicted in black and white for purposes of this application. In practice, the image is colored, with color carrying additional information on periodicity of features in the silicon film. Blue and green tones are dominant under common conditions, but this should not be considered as limiting the present invention.

Figure 3:
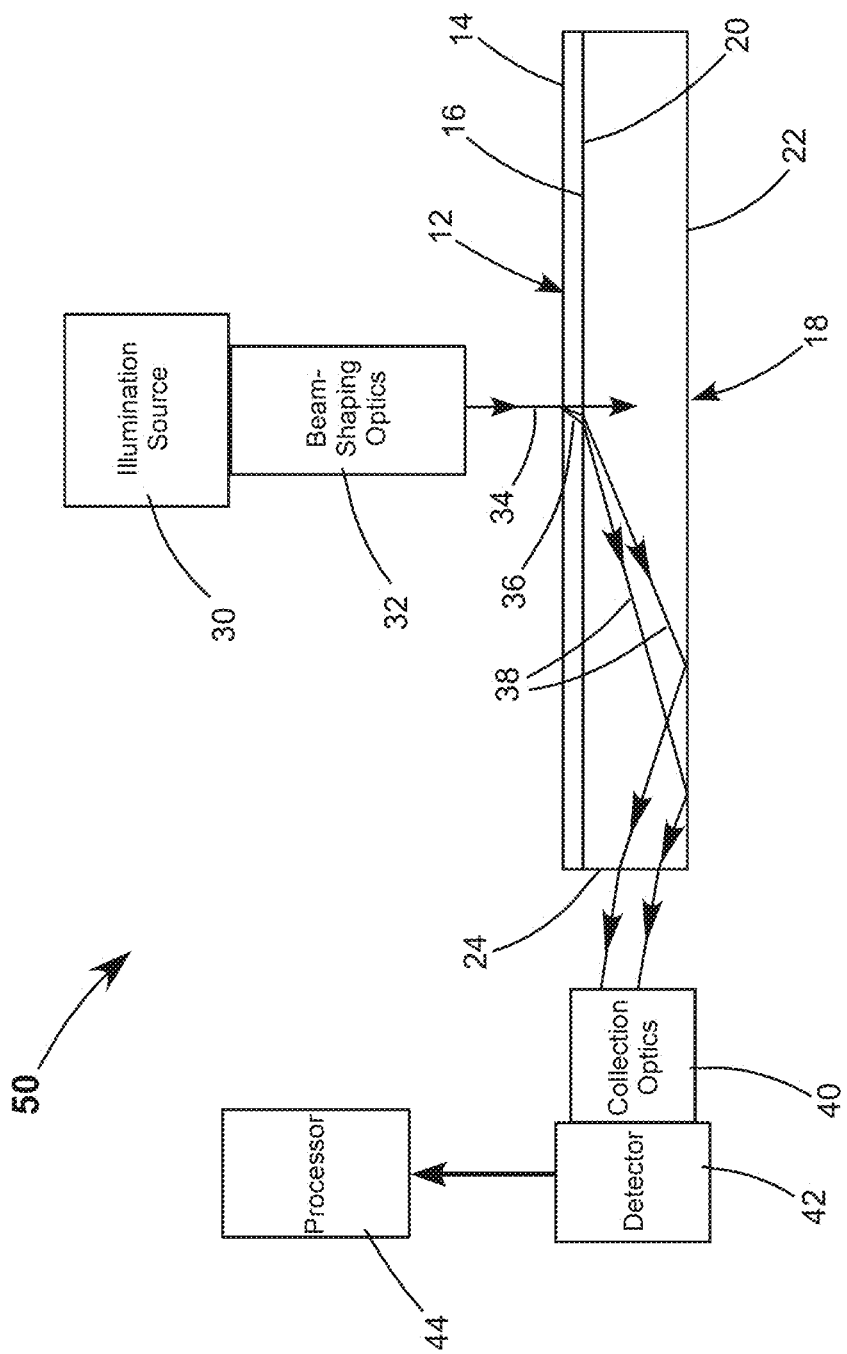
FIG. 3 schematically illustrates another preferred embodiment of the present invention for evaluating a silicon layer on a transparent substrate, including an illumination source and beam-shaping optics directing light into the substrate by diffraction from the silicon layer, collection optics for collecting a portion of the light diffracted into the substrate, wave-guided along the substrate and exiting the substrate via an edge thereof, and a detector element and processor for monitoring the diffracted light portion.

FIG. 3 schematically illustrates another preferred embodiment 50 of the present invention for evaluating a silicon layer 12 on a substrate 18. In this embodiment, illumination source 30 and beam-shaping optics 32 direct light rays 34 onto upper surface 14 of silicon layer 12. Periodic surface features in the silicon layer diffract light into substrate 18, as depicted by diffracted rays 36. At least a portion of the light diffracted into substrate 18 is wave-guided thereby, as depicted by diffracted-and-guided rays 38. Diffracted and guided light exits the substrate through edge 24 thereof and is delivered to detector 42 by collection optics 40. Light rays 34 are incident on substrate 18 such that light that is not diffracted will not be guided by the substrate, thereby achieving the desired decoupling of the illuminating source from the detector.

Figure 4:
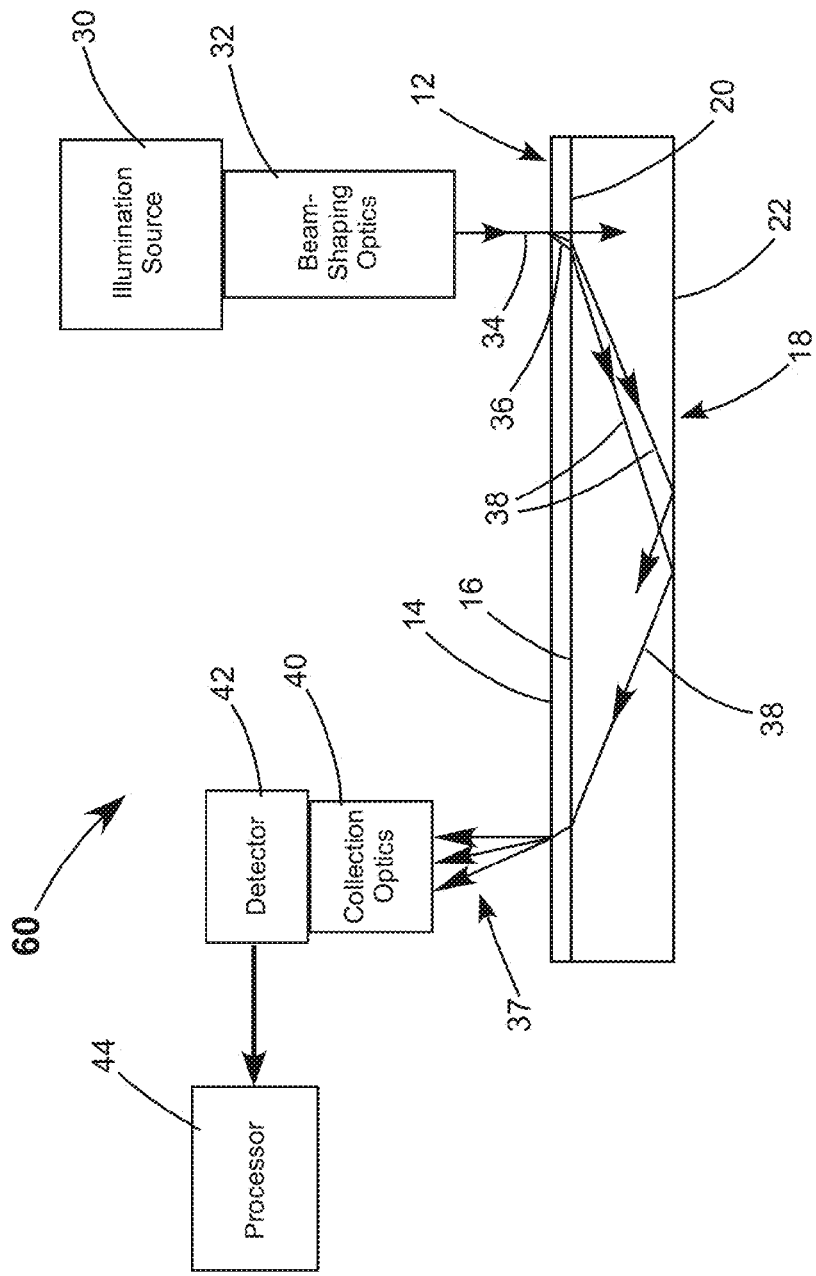
FIG. 4 schematically illustrates yet another preferred embodiment of the present invention for evaluating a silicon layer on a transparent substrate, including an illumination source and beam-shaping optics directing light into the substrate by diffraction from the silicon layer thereon at a first location, collection optics adjacent a second location on the substrate for collecting a portion of the light diffracted into the substrate, wave-guided along the substrate and diffracted out of the substrate at the second location by the silicon layer thereon, and a detector element and processor for monitoring the light portion diffracted out of the substrate at the second location.

FIG. 4 schematically illustrates another preferred embodiment 60 of the present invention for evaluating a silicon layer 12 on a substrate 18. In this embodiment, illumination source 30 and beam-shaping optics 32 direct light rays 34 onto an illuminated location of silicon layer 12, as in embodiment 50 of FIG. 3. Collection optics 40 and detector 42 are arranged to receive light propagating from a detected location of silicon layer 12, as in embodiment 10 of FIG. 1. Periodic surface features in the illuminated location diffract a portion of rays 34 into substrate 18, wherein they are wave-guided thereby, as depicted by diffracted rays 36 and diffracted-and-guided rays 38. Similarly, periodic surface features in the detected location diffract a portion of diffracted-and-guided rays 38 out of silicon layer 12, as depicted by diffracted rays 37.

Silicon layer 12 may be evaluated by translating the illuminated location, while monitoring diffracted rays 37 propagating from a detected location that is stationary. In another mode, the detected location is translated, while light rays 34 are directed onto an illuminated location that is stationary. To maximize the area of a substrate accessible to the translated location, it is convenient to select a stationary location towards the edge of the substrate. In yet another mode, the illuminated location and the detected location are both translated in lockstep. Light rays 34 are generated by illumination source 30 and directed by beam-shaping optics 32 as described above. Diffracted rays 37 are monitored as described above using collection optics 40, detector 42, and processor 44.

Figure 5:
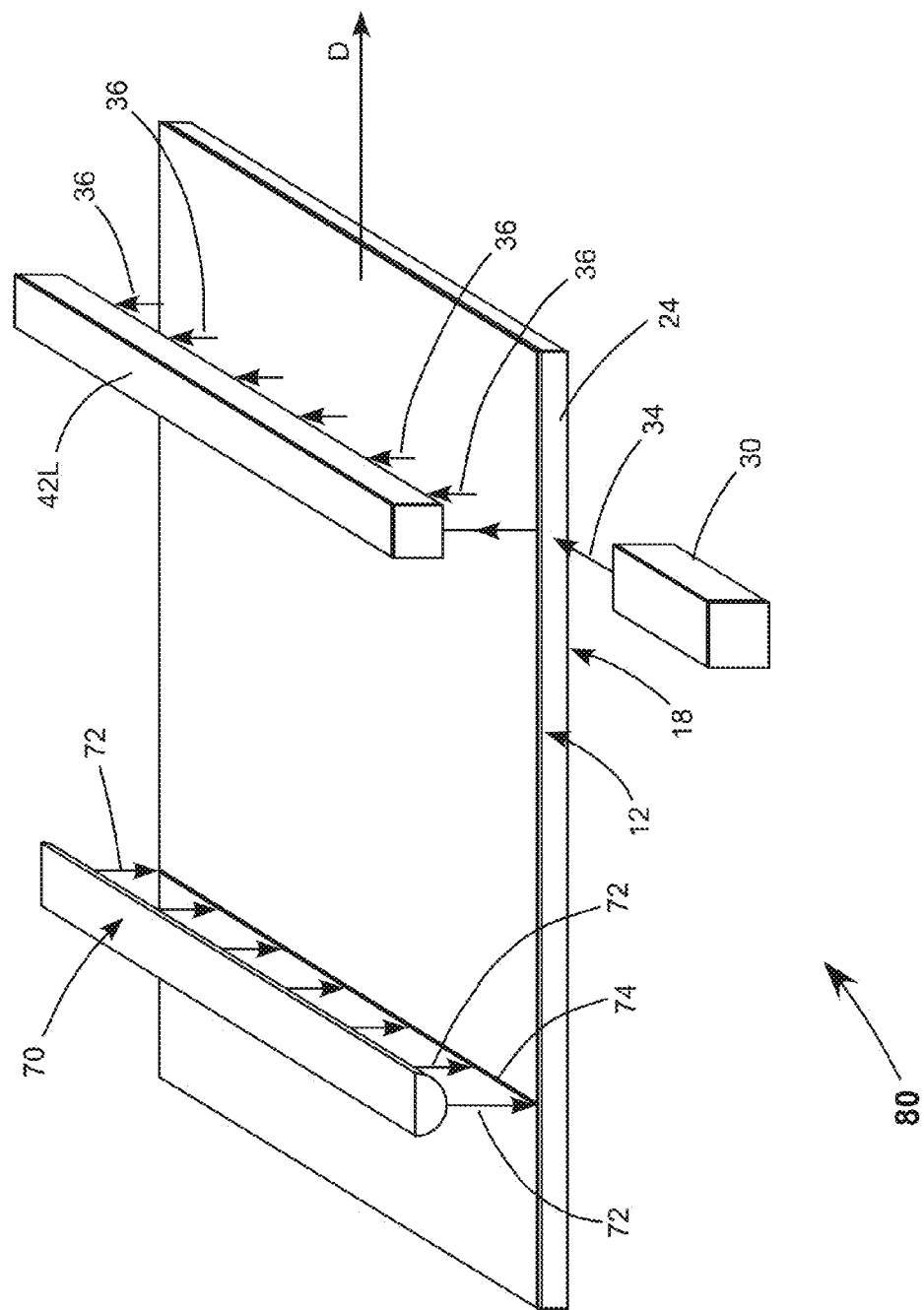
FIG. 5 is a three-dimensional view schematically illustrating an arrangement in accordance with the present invention for recording a large area image in diffracted light of a silicon layer being recrystallized, wherein the diffracted light is generated using principles of the embodiment of FIG. 1.

FIG. 5 schematically illustrates an arrangement 80 in accordance with the present invention for recording a large area image in diffracted light of a silicon layer 12 being recrystallized. The diffracted light is generated using principles of the embodiment of FIG. 1. Recrystallization is effected by focusing laser-radiation from an excimer laser (not shown) onto silicon layer 12 using an elongated lens 70. Lens 70 focuses rays 72 from the excimer laser (not shown) to form an elongated beam (line-beam) 74. Substrate 18, with silicon layer 12 thereon, is translated (scanned) in a direction perpendicular to line-beam 74 as indicated by arrow D.

Light from illumination source 30 is injected into substrate 18, through edge 24 thereof, in a direction perpendicular to the scan direction. Injected light rays 34 are wave-guided across substrate 18 and diffracted rays 36 are formed by periodic surface features in silicon layer 12, as described above in the above description of the embodiment of FIG. 1. Beam-shaping optics and collection optics are not shown in the drawing for simplicity of illustration.

Diffracted rays 36 are directed into a detector array 42L extending across the substrate. Detector array 42L provides an image of a linear portion of the silicon layer being recrystallized. A series of such images can be combined by the processor (not shown) to form an image of at least a large portion of the area, if not the entire area, of the silicon layer.

In summary, the present invention is directed to a method of evaluating a silicon layer being crystallized by excimer-laser annealing. Light from an illumination source is injected into the substrate. Light is diffracted out of the substrate by periodic surface features in the silicon layer is monitored by a detector. The illumination source is completely de-coupled from the detector. The invention may be integrated into a crystallization apparatus and crystallization process for in-line evaluation of the crystallized silicon layer, or used separately for off-line evaluation and analysis.

The invention is described above with reference to a preferred and other embodiments. In any of the embodiments described above, light may be directed into the substrate from a plurality of illumination sources, to maximize the area of a panel illuminated and therefore accessible for monitoring. In any of the embodiments described above, either the electrical signal directly from the detector or the electrical signal interpreted by the processor can be used to control the excimer laser and thereby optimize the crystallization process. The invention is not limited, however, to the embodiments described and depicted. Rather, the invention is limited only by the claims appended hereto.

What is claimed is:

1. A method of detecting periodic surface features in a recrystallized silicon layer provided on a substrate, the method comprising:
   coupling light into the substrate at a first location such that at least a portion of the light is wave-guided by the substrate and coupled out of the substrate at a second location; and
   monitoring the light coupled out of the substrate to determine properties of the periodic surface features.

2. The method of claim 1, wherein the light is coupled into the substrate via an edge thereof and the light is coupled out of the substrate at a surface thereof by the periodic surface features.

3. The method of claim 1, wherein the light is coupled into the substrate at the surface thereof by the periodic surface features and coupled out of the substrate at an edge thereof.

4. The method of claim 1, wherein the light is coupled into the substrate at a first location of the surface of the substrate by the periodic surface features and coupled out of the substrate at a second location of the surface of the substrate by the periodic surface features.

5. The method of claim 1, wherein light is coupled out of the substrate by diffraction from the periodic surface features.

6. The method of claim 1, wherein properties of the periodic surface features are evaluated through contrast in the light coupled out of the substrate.

7. The method of claim 1, wherein properties of the periodic surface features are evaluated through spectral content of the light coupled out of the substrate.

8. The method of claim 1, wherein the periodic surface features are introduced into the the recrystallized silicon layer by an excimer-laser annealing process.

9. The method of claim 1, wherein the light coupled into the substrate is visible light.

10. The method of claim 1, wherein the monitoring step is performed by collection optics receiving the light coupled out of the substrate and directing that light onto a detector.

11. The method of claim 10, wherein the collection optics are an optical microscope.

12. The method of claim 10, wherein the detector is a digital camera.

13. The method of claim 10, wherein an electrical signal from the detector is received and interpreted by a processor to obtain a numerical representation of the condition of the silicon layer.

14. The method of claim 13, wherein the electrical signal is a digital image.

15. The method of claim 13, wherein the electrical signal is used to control a laser and thereby optimize a recrystallization process.

16. The method according to claim 13, wherein the electrical signal interpreted by the processor is used to control a laser and thereby optimize a recrystallization process.

17. An apparatus for evaluating a silicon layer on a substrate, wherein the silicon layer includes periodic surface features formed during an annealing process, said apparatus comprising:
- an illumination source for injecting light into an edge of the substrate so that the light is wave-guided by the substrate;
- collection optics positioned adjacent the surface of the silicon layer for collecting a portion of the injected light that is coupled out of the substrate by the periodic surface features and forming an optical image;
- a detector for converting the optical image formed by the collection optics into an electrical signal; and
- a processor for receiving and interpreting the electrical signal from the detector to obtain a numerical representation of the condition of the silicon layer.

18. The apparatus of claim 17, wherein the processor analyzes contrast in the light coupled out of the substrate.

19. The apparatus claim 17, wherein the processor analyzes spectral content of the light coupled out of the substrate.

20. The apparatus of claim 17, wherein the electrical signal interpreted by the processor is used to evaluate the annealing process.

* * * * *